US010729653B2

(12) United States Patent
Cuypers et al.

(10) Patent No.: US 10,729,653 B2
(45) Date of Patent: *Aug. 4, 2020

(54) PHARMACEUTICAL COMPOSITIONS COMPRISING 2-OXO-1-PYRROLIDINE DERIVATIVES

(75) Inventors: Serge Cuypers, Brussels (BE); Monique Berwaer, Brussels (BE); Domenico Fanara, Brussels (BE); Valery Barillaro, Brussels (BE)

(73) Assignee: UCB BIOPHARMA SRL, Brussels (BE)

(*) Notice: Subject to any disclaimer, the term of this patent is extended or adjusted under 35 U.S.C. 154(b) by 72 days.

This patent is subject to a terminal disclaimer.

(21) Appl. No.: 13/146,074

(22) PCT Filed: Jan. 27, 2010

(86) PCT No.: PCT/EP2010/050892
§ 371 (c)(1),
(2), (4) Date: Jul. 25, 2011

(87) PCT Pub. No.: WO2010/094535
PCT Pub. Date: Aug. 26, 2010

(65) Prior Publication Data
US 2011/0281929 A1    Nov. 17, 2011

(30) Foreign Application Priority Data
Jan. 29, 2009  (EP) .................................... 09100083

(51) Int. Cl.
| | | |
|---|---|---|
| *A61K 9/16* | (2006.01) | |
| *A61K 9/28* | (2006.01) | |
| *A61K 9/20* | (2006.01) | |
| *A61P 25/00* | (2006.01) | |
| *A61K 31/4015* | (2006.01) | |
| *A61P 25/08* | (2006.01) | |

(52) U.S. Cl.
CPC .......... *A61K 9/1623* (2013.01); *A61K 9/1652* (2013.01); *A61K 9/205* (2013.01); *A61K 9/2018* (2013.01); *A61K 9/2866* (2013.01); *A61K 31/4015* (2013.01); *A61P 25/00* (2018.01); *A61P 25/08* (2018.01)

(58) Field of Classification Search
CPC ............. A61K 31/4015; A61K 9/1623; A61K 9/1652; A61K 9/2018; A61K 9/205; A61K 9/2866; A61P 25/00; A61P 25/04; A61P 25/08
See application file for complete search history.

(56) References Cited

U.S. PATENT DOCUMENTS 5,807,576 A * 9/1998 Allen, Jr. ............. A61K 9/0056
424/465
2003/0004182 A1* 1/2003 Gierer .......................... 514/307

FOREIGN PATENT DOCUMENTS

| JP | 2005-298338 A | 10/2005 |
|---|---|---|
| WO | 06/131322 A | 12/2006 |
| WO | WO 2007/012439 A1 * | 2/2007 |
| WO | 2007/141002 A1 | 12/2007 |
| WO | 2008/027993 A2 | 3/2008 |

OTHER PUBLICATIONS

U.S. Appl. No. 13/144,895, filed Jul. 2011, Cuypers et al.*
Zhihong et al., "Preparation of beta-cyclodextrin clathrate of aniracetam", Journal of Shangdong Pharmaceutical Industry, 2003, 22(5), 3 pages.
"Aniracetam", Product Information, SIGMA, 1 page, Dec. 2003.
U.S. National Institutes of Health, "Clinical Study in Health Volunteers to Investigate the Neurocognitive Effects of a New Antiepileptic Drug: Brivaracetam", ClinicalTrialsFeeds.org.
XP002572305, 2008, retrieved from internet clinicaltrialsfeeds.org/clinica 1-trials/show/NCT00736931.
Shangraw, R. et al., "Characterization of the tableting properties of [beta]-cyclodextrin and the effects of processing variables on inclusion complex formation, compactibility and dissolution", Drug Development an Industrial Pharmacy, 1992, 18(17), 1831-1851.
Li et al., "Use of beta-cyclodextrin and derivatives thereof in pharmaceutics"; Chinese Journal of Information on TCM, Mar. 2005, vol. 12, N° 3, pp. 100-101.
Rowe et al., "Cyclodextrins", Handbook of Pharmaceutical Excipients, Pharmaceutical Press, 2006, 217-221.
Brivaracetam Formulation Report generated by UCB Jul. 2017.

* cited by examiner

*Primary Examiner* — Kara R McMillian
(74) *Attorney, Agent, or Firm* — McDonnell Boehnen Hulbert & Berghoff LLP

(57) ABSTRACT

The present invention relates to an immediate release formulation of pharmaceutical compounds.

14 Claims, No Drawings

PHARMACEUTICAL COMPOSITIONS COMPRISING 2-OXO-1-PYRROLIDINE DERIVATIVES

This application is a US national phase of International Application No. PCT/EP2010/050892 filed on Jan. 27, 2010, the disclosure of which is incorporated herein by reference in its entirety.

The present invention relates to a pharmaceutical composition of 2-oxo-1-pyrrolodine derivatives, a process of the preparation thereof and therapeutic uses thereof.

International patent application having publication number WO 01/62726 discloses 2-oxo-1-pyrrolidine derivatives and methods for their preparation. It particularly discloses compound (2S)-2-[(4R)-2-oxo-4-propyl-pyrrolidin-1-yl]butanamide known under the international non propriety name of Brivaracetam.

International patent application having publication number WO 2005/121082 describes a process of preparation of 2-oxo-1-pyrrolidine derivatives and particularly discloses a process of preparation of (2S)-2-[(4S)-4-(2,2-difluorovinyl)-2-oxo-pyrrolidin-1-yl]butanamide known under the international non propriety name of Seletracetam.

2-oxo-1-pyrrolidine derivatives are therefore particularly useful in the pharmaceutical industry.

Brivaracetam is effective in the treatment of epilepsy. A clinical trial evaluated the efficacy and safety of Brivaracetam (5, 20 and 50 mg per day) in the adjunctive treatment of adult patients with refractory partial onset seizures, with or without secondary generalization. Brivaracetam is also effective in the treatment of patients with post-herpetic neuralgia.

Seletracetam is effective in the treatment of epilepsy. Two studies were conducted with Seletracetam in epilepsy evaluating the efficacy and safety of Seletracetam in the adjunctive treatment of partial onset seizures in highly refractory adult patients currently receiving up to three concomitant anti-epileptic drugs.

One of the objectives of the invention is a pharmaceutical composition which can be administered orally to obtain an immediate release of pharmaceutically active substances.

Considering Brivaracetam and Seletracetam are classified as BCS I, the resulting in vitro dissolution (USP <711> apparatus n°2) according to the Guidance for Industry Immediate Release Solid Oral Dosage Forms the composition, In Vitro Dissolution Testing, (Center for Drug Evaluation and Research November 1995) should meet the criterion of the test described in the Case A of the Dissolution Documentation: Dissolution of 85% in 15 minutes in 900 mL of 0.1 N HCl. If it fails it should meet the test described in Case B or C.

As a general rule the term "Immediate Release" is understood here as not being a modified or controlled released and having an in-vitro dissolution release (USP <711> apparatus n°2) of at least 75% in 45 min in an appropriate buffered aqueous media.

The present invention relates to an oral pharmaceutical composition comprising particles, said particles comprising an active ingredient and 0.1% to 60% per weight of at least a cyclodextrin agent, with respect to the total weight of the particles, the active ingredient being an 2-oxo-1-pyrrolidine derivative of formula (I),

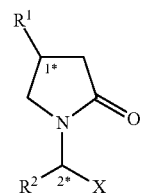

wherein,
$R^1$ is $C_{1-10}$ alkyl or $C_{2-6}$ alkenyl;
$R^2$ is $C_{1-10}$ alkyl or $C_{2-6}$ alkenyl;
X is —$CONR^4R^5$, —COOH, —$COOR^3$ or —CN;
$R^3$ is $C_{1-10}$ alkyl;
$R^4$ is hydrogen or $C_{1-10}$ alkyl;
$R^5$ is hydrogen or $C_{1-10}$ alkyl.

The term "active ingredient" as used herein is defined as a substance or a drug which has a therapeutic effect. It can also be a mixture of substances having a therapeutic effect.

The amount of the active ingredient present in the pharmaceutical composition of the invention may vary depending on the patient to which the compositions are administered and the disease to be treated.

The oral composition of the invention is in a solid form.

The term "alkyl", as used herein, is a group which represents saturated, monovalent hydrocarbon radicals having straight (unbranched), branched or cyclic moieties, or combinations thereof. Preferred alkyl comprises 1 to 10 carbons. More preferred alkyl comprises 1 to 4 carbons. Optionally, alkyl groups may be substituted by 1 to 5 substituents independently selected from the group consisting of halogen, hydroxy, alkoxy, ester, acyl, cyano, acyloxy, acid, amide or amino group. Preferred alkyl groups are methyl, ethyl, n-propyl, trifluoromethyl and trifluoroethyl.

The term "alkenyl" as used herein represents unsubstituted or substituted branched, unbranched or cyclic hydrocarbon radicals or combinations thereof having at least one double bond. Preferred alkenyl comprises 2 to 6 carbons. More preferred alkenyl comprises 2 to 4 carbons. "Alkenyl" moieties may be optionally substituted by 1 to 5 substituents independently selected from the group consisting of halogen, hydroxy, alkoxy, ester, acyl, cyano, acyloxy, carboxylic acid, amide or amino group.

The term "halogen", as used herein, represents an atom of fluorine, chlorine, bromine, or iodine.

The term "hydroxy", as used herein, represents a group of formula —OH.

The term "alkoxy", as used herein, represents a group of formula —$OR^a$ wherein $R^a$ is $C_{1-4}$ alkyl as defined above.

The term "acyl" as used herein, represents a group of formula $R^bCO$—, wherein $R^b$ represents a $C_{1-4}$ alkyl as defined above.

The term "ester", as used herein, represents a group of formula —$COOR^c$ wherein $R^c$ represents a $C_{1-4}$ alkyl as defined above.

The term "cyano" as used herein represents a group of formula —CN.

The term "acyloxy" as used herein represents a group of formula —O—$COR^d$, wherein $R^d$ is a $C_{1-4}$ alkyl as defined above or an aryl group.

The term "aryl" as used herein, represents an organic radical derived from an aromatic hydrocarbon by removal of one hydrogen, for example a phenyl.

The term "carboxylic acid" as used herein represents a group of formula —COOH.

The term "amino group", as used herein, represents a group of formula —$NH_2$, $NHR^e$ or $NR^fR^e$ wherein $R^e$ and $R^f$ are alkyl groups as defined above in the specification.

The term "amide", as used herein, refers to a group of formula —CO—$NH_2$, —CO—$NHR^g$, or —CO—$NR^gR^h$, wherein $R^g$ and $R^h$ are alkyl groups as defined above in the specification.

The term "sulfonate group" as used herein represents a group of formula —O—$SO_2$—$R^i$ wherein $R^i$ is an alkyl or an aryl as defined here above in the specification. Preferred sulfonate groups are methanesulfonate, para-toluenesulfonate group or trifluoromethanesulfonate.

In one embodiment, according to first aspect of the present invention, $R^1$ is H, $C_{1-4}$ alkyl or $C_{2-4}$ alkenyl. In a further embodiment according to first aspect of the present invention, $R^1$ is hydrogen, n-propyl or 2,2-difluorovinyl.

In one embodiment according to first aspect of the present invention, $R^2$ is $C_{1-4}$ alkyl. In another embodiment according to first aspect of the present invention, $R^2$ is ethyl.

In one embodiment according to first aspect of the present invention, X is —$CONR^4R^5$, —COOH or —$COOR^3$, wherein $R^3$ is a $C_{1-4}$ alkyl. In another embodiment according to first aspect of the present invention, X is —$CONR^4R^5$.

In one embodiment according to first aspect of the present invention, $X^1$ is —$CONR^4R^5$ or —$COOR^3$, wherein $R^3$ is a $C_{1-4}$ alkyl. In another embodiment according to first aspect of the present invention, $X^1$ is $COOR^3$, wherein $R^3$ is a $C_{1-4}$ alkyl.

In one embodiment according to first aspect of the present invention, $X^2$ is —$CONR^4R^5$ or —$COOR^3$, wherein $R^3$ is a $C_{1-4}$ alkyl. In another embodiment according to first aspect of the present invention, $X^2$ is $COOR^3$, wherein $R^3$ is a $C_{1-4}$ alkyl.

In a particular embodiment, $R^3$ is methyl.

In one embodiment according to first aspect of the present invention, $R^4$ is hydrogen or $C_{1-4}$ alkyl. In another embodiment according to first aspect of the present invention, $R^4$ is hydrogen.

In one embodiment according to first aspect of the present invention, $R^5$ is hydrogen or $C_{1-4}$ alkyl. In another embodiment according to the first aspect of the present invention, $R^5$ is hydrogen.

Preferably $R^1$ is n-propyl or 2,2-difluorovinyl; $R^2$ is ethyl; and X is —$CONH_2$.

More preferably, the active ingredient is chosen among brivaracetam and seletracetam. Best results have been obtained with brivaracetam.

The term "particles" includes granules, microgranules, microparticles, pellets.

Usually, the pharmaceutical composition of the invention contains particles, said particles comprising at least an active ingredient and at least a cyclodextrin agent. There are various types of pharmaceutical compositions containing particles such as tablet, powder, granule, capsules. Particles can also be in a sachet, such as a sachet containing a dose of active ingredient. So the preparation is handy, and can be divided and dosed very easily.

The term "cyclodextrin agent" as used herein is defined as a pharmaceutical acceptable excipient which is a cyclic oligosaccharide created by 6, 7 or 8 alpha-D-glucopyranose units, commonly known as alpha, beta or gamma cyclodextrin respectively. It is added as a compacting agent. Usually, the cyclodextrin agent is chosen among alpha cyclodextrin, beta cyclodextrin, hydroxypropyl beta cyclodextrin, methyl beta cyclodextrin, sulfobutyl beta cyclodextrin, gamma cyclodextrin, and hydroxypropyl gamma cyclodextrin. Generally, the cyclodextrin agent is a beta cyclodextrin. Preferably, the cyclodextrin agent is a beta cyclodextrin having a crystalline structure by contrast to amorphous cyclodextrin. In a preferred embodiment, the cyclodextrin agent is a beta cyclodextrin having a water content between 4 and 18%, and preferably between 5 and 16% (w/w), and more preferably between 10 and 16% (w/w). The best results have been obtained with a beta cyclodextrin having a water content between 10 and 14% (w/w).

More preferably, the cyclodextrin agent is the beta cyclodextrin sold under the trademark Kleptose® or Betadex®, or Cavamax® W7.

Usually, the pharmaceutical composition according to the present invention comprises 0.1 to 50% per weight of cyclodextrin agent with respect to the total weight of the particles. Particularly, the pharmaceutical composition comprises 0.1 to 45% per weight of cyclodextrin agent. Preferably, the pharmaceutical composition comprises 0.5 to 40% per weight of cyclodextrin agent; more preferably 1.0 to 30% per weight of cyclodextrin agent; and most preferably 1.0 to 15.0% per weight of cyclodextrin agent with respect to the weight of the particles. The best results have been obtained in the range of 4.0 to 11.0% per weight of cyclodextrin agent.

The particles of the invention may also comprise a disintegrant, a diluent, a processing aid, a lubricant, a gliding agent and a mixture therefore, as excipient.

The particles of the invention may comprise a disintegrant, as excipient.

The term "disintegrant" as used herein is defined as an accelerating agent of the disintegration of the tablet and the dispersion of the active ingredient in water or gastrointestinal fluids. The disintegrant may be present in the pharmaceutical composition in the form of a single compound or in the form of a mixture of compounds.

Examples of disintegrant are starches, pregelatinized starch, sodium croscarmellose, also referred to as cross-linked sodium carboxymethylcellulose, and cross-linked polyvinylpyrrolidone. Preferred disintegrants according to the present invention are cross-linked polyvinylpyrrolidone, sodium starch glycolate and sodium croscarmellose. More preferred disintegrant is sodium croscarmellose (crosslinked carboxymethylcellulose sodium).

Preferably, the particles according to the present invention comprise 0.5 to 25% per weight of disintegrant, more preferably 1.0 to 15% per weight of disintegrant, most preferably 1.5 to 8% per weight of disintegrant, with respect to the weight of the particles. The best results have been obtained in the range of 2.0 to 5% per weight of disintegrant.

The particles of the invention may also comprise diluents as excipient.

The term "diluent" as used herein is defined as an agent used as filler in order to achieve the desired composition volume or weight. The diluent may be present in the pharmaceutical composition within granules in the form of a single compound or in the form of a mixture of compounds.

Examples of diluent are, but not limited to, lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose. Preferred diluents are lactose and starch. More preferably diluent is lactose monohydrate, anhydrous lactose or a mixture thereof. The best results have been obtained with lactose monohydrate.

Usually, the particles according to the present invention comprise 5 to 95% per weight of diluent with respect to the weight of the particles. Preferably, the particles comprise 10 to 90% per weight of diluent with respect to the total weight of the particles. More preferably, the particles comprise 30 to 90% per weight of diluent with respect to the weight of the particles.

The particles of the invention may also comprise lubricant as excipient.

Examples of lubricants are, but not limited to, talc, magnesium stearate, calcium stearate, poloxamer, sodium lauryl sulfate, stearic acid, hydrogenated castor oil. Preferred lubricant according to the present invention is magnesium stearate.

Usually, the particles according to the present invention comprise 0 to 5.50% per weight of lubricant with respect to the total weight of the particles. Preferably, the particles comprise 0.001 to 2.50% per weight of lubricant. More preferably, the particles comprise 0.01 to 2.0% per weight of lubricant with respect to the total weight of the particles.

The present invention preferentially comprises said particles as a dispersed phase into a solid continuous phase, external to the granules. Said solid external phase can be a matrix phase (for instance in a tablet) or a blend of excipients (for instance in a capsule or a sachet).

The particles of the invention may also be comprised in an external phase comprising other inactive ingredients such as a disintegrant, a diluent, a processing aid, a lubricant, a gliding agent and a mixture thereof, as excipient. The particles are mixed with an external phase.

Examples of lubricants are, but not limited to, talc, magnesium stearate, calcium stearate, poloxamer, sodium lauryl sulfate, stearic acid, hydrogenated castor oil. Preferred lubricant according to the present invention is magnesium stearate.

Usually, the pharmaceutical composition according to the present invention comprises 0 to 5.50% per weight of lubricant with respect to the total weight of the composition. Preferably, the pharmaceutical composition comprises 0.5 to 2.50% per weight of lubricant. More preferably, the pharmaceutical composition comprises 0.5 to 2.0% per weight of lubricant with respect to the total weight of the composition.

The pharmaceutical composition of the invention may comprise a disintegrant, as excipient.

Examples of disintegrant are starches, pregelatinized starch, sodium croscarmellose, also referred to as cross-linked sodium carboxymethylcellulose, and polyvinylpyrrolidone. Preferred disintegrants according to the present invention are polyvinylpyrrolidone, sodium starch glycolate and sodium croscarmellose. More preferred disintegrant is sodium croscarmellose (crosslinked carboxymethylcellulose sodium).

Preferably, the pharmaceutical composition according to the present invention comprises 0 to 7.0% per weight of disintegrant, more preferably 1.5 to 6.0% per weight of disintegrant, most preferably 3.0 to 5.0% per weight of disintegrant, with respect to the total weight of the composition.

The pharmaceutical composition of the invention may also comprise in an external phase. The external phase may comprise diluents, lubricant, and/or gliding agent as excipient. Preferably the external phase does not comprise an active ingredient.

Examples of diluent are, but not limited to, lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose. Preferred diluents are lactose and starch. More preferably diluent is lactose monohydrate, anhydrous lactose or a mixture thereof. The best results have been obtained with anhydrous lactose.

Usually, the pharmaceutical composition according to the present invention comprises 5 to 90% per weight of diluent with respect to the total weight of the composition. Preferably, it comprises 10 to 90% per weight of diluent. More preferably, it comprises 15 to 60% per weight of diluent with respect to the total weight of the composition.

The external phase of the pharmaceutical composition of the invention may also comprise a lubricant.

Examples of lubricants are, but not limited to, talc, magnesium stearate, calcium stearate, poloxamer, sodium lauryl sulfate, stearic acid, hydrogenated castor oil. Preferred lubricant according to the present invention is magnesium stearate.

Usually, the pharmaceutical composition according to the present invention comprises 0.25 to 5.50% per weight of lubricant with respect to the total weight of the composition. Preferably, it comprises 0.5 to 2.50% per weight of lubricant. More preferably, it comprises 0.5 to 2.0% per weight of lubricant with respect to the total weight of the composition.

The external phase of the pharmaceutical composition may also comprise a gliding agent.

Examples of gliding agents are, but not limited to colloidal silicon dioxide and talc. Preferred gliding agent according to the present invention is colloidal silicon dioxide.

Usually, the pharmaceutical composition according to the present invention comprises 0 to 5.00% per weight of gliding agent with respect to the total weight of the composition. Preferably, the composition comprises 0 to 2.50% per weight of gliding agent. More preferably, the composition comprises 0 to 2.0% per weight of gliding agent with respect to the total weight of the composition.

In one embodiment of the invention, the pharmaceutical composition comprises particles, said particles comprising brivaracetam as active ingredient and 0.1% to 60% per weight of at least a cyclodextrin agent, with respect to the total weight of the particles. Particularly, the pharmaceutical composition comprises particles, said particles comprising Brivaracetam as active ingredient;
0.1 to 60% per weight of at least a cyclodextrin agent;
0.5 to 25% per weight of disintegrant; and
5 to 95% per weight of diluent; with respect to the total weight of the particles.

Particularly, the pharmaceutical composition comprises particles, said particles comprising Brivaracetam as active ingredient;
0.1 to 50% per weight of at least a cyclodextrin agent;
1.0 to 15% per weight of disintegrant; and
10 to 90% per weight of diluent; with respect to the total weight of the particles.

Particularly, the pharmaceutical composition comprises particles, said particles comprising Brivaracetam as active ingredient;
1.0 to 30% per weight of at least a cyclodextrin agent;
1.5 to 8% per weight of disintegrant; and
30 to 90% per weight of diluent; with respect to the total weight of the particles.

In another embodiment of the invention, the pharmaceutical composition comprises particles, said particles comprising brivaracetam, as active ingredient; 0.1 to 60% per weight of at least a cyclodextrin agent with respect to the total weight of the particles; sodium croscarmellose; and lactose monohydrate.

Particularly, the pharmaceutical composition comprises particles, said particles comprising
Brivaracetam as active ingredient;
0.1 to 60% per weight of at least a cyclodextrin agent;
0.5 to 25% per weight of sodium croscarmellose; and
5 to 95% per weight of lactose monohydrate; with respect to the total weight of the particles.

Particularly, the pharmaceutical composition comprises particles, said particles comprising
Brivaracetam as active ingredient;
0.1 to 50% per weight of at least a cyclodextrin agent;
2.0 to 15% per weight of sodium croscarmellose; and
10 to 90% per weight of lactose monohydrate; with respect to the total weight of the particles.

Particularly, the pharmaceutical composition comprises particles, said particles comprising
Brivaracetam as active ingredient;
1.0 to 30% per weight of at least a cyclodextrin agent;
2.0 to 8% per weight of sodium croscarmellose; and
30 to 90% per weight of lactose monohydrate; with respect to the total weight of the particles.

In a preferred embodiment of the invention, the composition comprises particles, said particles comprising 10.00 mg of brivaracetam, 2.70 mg of beta cyclodextrin, 19.40 mg of lactose monohydrate and 1.00 mg of sodium croscarmellose.

In a preferred embodiment of the invention, the composition comprises particles, said particles comprising 10.00 mg of brivaracetam, 2.70 mg of beta cyclodextrin, 19.30 mg of anhydrous lactose, 19.40 mg of monohydrate lactose and 2.00 mg of sodium croscarmellose.

In a preferred embodiment of the invention, the composition comprises particles, said particles comprising 25.00 mg of brivaracetam, 6.75 mg of beta cyclodextrin, 48.50 mg of lactose and 2.50 mg of sodium croscarmellose.

In a preferred embodiment of the invention, the composition comprises particles, said particles comprising 50.00 mg of brivaracetam, 13.50 mg of beta cyclodextrin, 97.00 mg of lactose and 5.00 mg of sodium croscarmellose.

In a preferred embodiment of the invention, the composition is a tablet which comprises particles and pharmaceutically acceptable additives, the particles comprising 10.00 mg of brivaracetam, 2.70 mg of beta cyclodextrin, 19.40 mg of lactose monohydrate and 1.00 mg of sodium croscarmellose; and the additives comprising 1.00 sodium croscarmellose, 19.30 mg of anhydrous lactose and 0.60 mg magnesium stearate.

In a preferred embodiment of the invention, the composition is a tablet which comprises particles and pharmaceutically acceptable additives, the particles comprising 10.00 mg of brivaracetam, 2.70 mg of beta cyclodextrin, 45.00 mg of lactose monohydrate and 2.00 mg of sodium croscarmellose; and in the external phase the additives comprising 2.00 sodium croscarmellose, 45.10 mg of anhydrous lactose and 1.20 mg magnesium stearate.

In a preferred embodiment of the invention, the composition is a tablet which comprises particles and pharmaceutically acceptable additives, the particles comprising 25.00 mg of brivaracetam, 6.75 mg of beta cyclodextrin, 48.50 mg of lactose monohydrate and 2.50 mg of sodium croscarmellose, and the additives comprising 2.50 sodium croscarmellose, 48.25 mg of anhydrous lactose and 1.50 mg magnesium stearate.

In a preferred embodiment of the invention, the composition is a tablet which comprises particles and pharmaceutically acceptable additives, the particles comprising 50.00 mg of brivaracetam, 13.50 mg of beta cyclodextrin, 97.00 mg of lactose monohydrate and 5.00 mg of sodium croscarmellose, and the additives comprising 5.00 sodium croscarmellose, 96.50 mg of anhydrous lactose and 3.00 mg magnesium stearate.

In a preferred embodiment of the invention, the composition is a tablet which comprises particles and pharmaceutically acceptable additives, the particles comprising 9.2 mg of brivaracetam, 2.50 mg of beta cyclodextrin, 41.5 mg of lactose monohydrate and 1.80 mg of sodium croscarmellose, and the additives comprising 1.80 sodium croscarmellose, 41.6 mg of anhydrous lactose, 0.5 mg silicon dioxide colloidal and 1.10 mg magnesium stearate.

The pharmaceutical composition of the invention is usually manufactured by dry granulation.

The process for preparing particles according to the invention comprises
a first step wherein the active ingredient, and cyclodextrin agent, and excipients, are mixed;
a second step wherein the resulting blend is compressed and for compacted; and
a third step wherein the blend is ground to obtain particles.

The process for preparing tablets according to then invention comprises
a fourth step wherein the obtained particles, and excipients are mixed; and
a fifth step wherein the final blend is compressed and for compacted in order to obtain tablets.

The manufacturing process by dry granulation comprises an initial mixing step of the active ingredient, and cyclodextrin agent, and a diluent and a disintegrant. The resulting blend is compressed using a roller compactor or a tabletting machine and then ground to obtain particles. The obtained particles, a diluent and a disintegrant are mixed with a blender, then a lubricant is added and mixed. The final blend is compressed in order to obtain tablets. Possibly the core tablets may be coated using a coating suspension or solution.

The particles comprise the active ingredient, the diluent, the cyclodextrin agent, and the disintegrant and possibly the lubricant. The particles are manufactured as follows: The active ingredient, the diluent, the cyclodextrin agent and the disintegrant are mixed using a planetary mixer. Then possibly the lubricant is added. The blend is mixed. This pre-blend is then compacted using a roller compactor and the resulting ribbons are sieved if necessary in order to obtain the particles. If tablet are requested, the particles are then mixed with the disintegrant and possibly with the lubricant. The final blend is then compressed on a tablet machine to obtain the tablets cores.

The main steps of the process for manufacturing tablets are as follows:
Blending the cyclodextrin agent, croscarmellose sodium, lactose monohydrate and the active ingredient: the blending operation can be achieved using diffusion mixers, convection mixers and/or pneumatic mixers.
Compaction: the compaction can be performed using a tablet press and/or a dry granulator by slugging or roller compaction.
Grinding: the grinding of the ribbons obtained by dry granulation can be performed using screening mills with a screen opening size comprised between 0.22 mm to 5 mm and more preferably between 0.33 mm to 4 mm.
Adding anhydrous lactose, croscarmellose sodium, and possibly magnesium stearate,
Blending: the blending operation can be achieved using diffusion mixers, convection mixers and/or pneumatic mixers.
Adding a lubricant (magnesium stearate) possibly.

Final blending.

Compression: the tabletting operation can be performed using a tablet press.

Film-coating: this operation can be performed using a pan coater or a gas suspension based coater and more preferably a perforated pan coater.

Cyclodextrin agent is used as a binder for dry granulation process surprisingly. No inclusion complexes are formed between the active ingredient and the cyclodextrin agent. The inventors have found a surprising binding effect of the cyclodextrin agent used in the pharmaceutical composition of the invention. The cyclodextrin agent reduces the sticking of the ribbons obtain after the compaction and provides defined particles after compaction.

When the pharmaceutical composition of the invention is a tablet, the process may comprise a further film-coating step in which water, preferably purified water, is added to the film-coating agent and resulting suspension and/or solution is sprayed on the tablet.

In another aspect the present invention relates to a pharmaceutical composition comprising Brivaracetam useful for the treatment or prevention of a disease.

By the term "disease", we understand a disease selected from the group consisting of epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, cluster headache, trigeminal and other neuralgia, chronic pain, neuropathic pain, cerebral ischemia, cardiac arrhythmia, myotonia, cocaine and other substance abuse (e.g. alcohol, benzodiazepines, opiates, marijuana, barbiturates, amphetamines, other stimulants), stroke, myoclonus, dystonia, dyskinesia, tremor, essential tremor, simple or complex tics, Tourette syndrome, restless leg syndrome and other movement disorders, neonatal cerebral haemorrhage, amyotrophic lateral sclerosis, spasticity and degenerative diseases.

The term "treatment" as used herein, includes curative treatment and prophylactic treatment.

By "curative" is meant efficacy in treating a current symptomatic episode of a disorder or condition.

By "prophylactic" is meant prevention of the occurrence or recurrence of a disorder or condition.

The present invention concerns also a method for treatment of a human patient by using the pharmaceutical composition.

The present invention concerns also the pharmaceutical composition for use as a medicament for curing the said disease.

The present invention concerns also the use of the pharmaceutical composition for the manufacture of a medicament for a therapeutic application in the said disease.

Preferably said disease is selected from the group consisting essentially of epilepsy, Parkinson's disease, dyskinesia, migraine, tremor, essential tremor, bipolar disorders, chronic pain, neuropathic pain, or bronchial, asthmatic or allergic conditions. More preferably said disease is epilepsy.

The dry granulation process used to prepare the pharmaceutical composition of the invention is easy, rapid, cost effective and may protect the active pharmaceutical ingredient form the degradation by hydrolysis for example.

The amount of excipients was aimed to be as low as possible in order to keep a low tablet weight.

Another advantage of the pharmaceutical composition of the invention resides in the fact that proportional formulations are possible, so the same blend could be compressed as tablet cores of increasing size and mass depending on the dosage needed.

Adding cyclodextrin agent in the pharmaceutical composition of the invention results in good compaction profiles, compression ability and/or finally in-vitro dissolution results. Cyclodextrin agent shows high compactibility results and does not require high compression pressures in order to produce tablets.

Brivaracetam is a very sticking compound (ability to adhere). The main advantage of cyclodextrin agent is to reduce sticking during compaction, and in particular rolling compaction.

Another advantage is to improve the drug dissolution.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

Example 1

A tablet is prepared by dry granulation process with the following composition (table 1).

TABLE 1

| composition 100 mg | |
|---|---|
| Components | tablet A % |
| Brivaracetam | 37.0 |
| Lactose monohydrate | 48.5 |
| Beta cyclodextrin | 10.0 |
| Sodium croscarmellose | 3.7 |
| Magnesium stearate | 0.8 |

The particles comprise the active ingredient, the diluent, the cyclodextrin agent and a part of the disintegrant and a part of the lubricant. The external phase comprises the second part of the disintegrant and the second part of the lubricant.

The particles are manufactured as follows. The brivaracetam as active ingredient, lactose monohydrate, the cyclodextrin agent and the half of the amount of sodium croscarmellose are mixed using the adequate blender. The blend is mixed until the achievement of a homogenous blend. This blend is then compacted using a compactor or a tablet machine and the resulting ribbons or raw tablet cores are sieved in order to obtain the particles. The particles are then mixed with the half of the amount of sodium croscarmellose and with the magnesium stearate in order to have an homogenous blend. The final blend is then compressed on a tablet machine to obtain the tablets cores.

TABLE 2

| results in % of 100 mg brivaracetam immediate release tablets (paddle method, 900 mL aqueous buffer, 50 rpm) | |
|---|---|
| Time (hours) | % Brivaracetam dissolved in comparison with the total weight of brivaracetam in the composition |
| 0 | 0 |
| 0:15:00 | 100 |

TABLE 2-continued results in % of 100 mg brivaracetam immediate release
tablets (paddle method, 900 mL aqueous buffer, 50 rpm)

| Time (hours) | % Brivaracetam dissolved in comparison with the total weight of brivaracetam in the composition |
|---|---|
| 0:30:00 | 100 |
| 0:45:00 | 100 |
| 1:00:00 | 100 |

Tablet 2 shows an immediate release of the Brivaracetam that complies with the in vitro dissolution requirements.

The in vitro dissolution profiles in water of tablets are determined according to the USP <711> (apparatus n° 2, 50 rpm, aqueous medium 900 mL, phosphate buffer pH 6). The dissolution was conducted at 37° C.

Adding cyclodextrin agent in the pharmaceutical composition of the invention results in good compaction profiles, compression ability. Cyclodextrin agent shows high compactibility results and does not require high compression pressures in order to produce tablets.

The cyclodextrin agent is able to reduce sticking during rolling compaction.

Example 2

A tablet is prepared by dry granulation process with the following composition (table 3).

TABLE 3 composition 5 mg

| Components | tablet B % |
|---|---|
| Brivaracetam | 9.3 |
| Anhydrous lactose | 41.8 |
| Lactose monohydrate | 41.7 |
| Beta cyclodextrin | 2.5 |
| Sodium croscarmellose | 3.7 |
| Magnesium stearate | 1.1 |

The particles are manufactured as follows. The brivaracetam as active ingredient, lactose monohydrate, the cyclodextrin agent and the half of the amount of sodium croscarmellose are mixed using the adequate blender. The blend is mixed until the achievement of a homogenous blend. This blend is then compacted using a compactor or a tablet machine and the resulting ribbons or raw tablet cores are sieved in order to obtain the particles. The particles are then mixed with the half of the amount of sodium croscarmellose, with the anhydrous lactose and the magnesium stearate in order to have a homogenous blend. The final blend is then compressed on a tablet machine to obtain the tablets cores.

Table 4 results in % of 5 mg brivaracetam immediate release tablets (paddle method, 500 mL, phosphate buffer pH 6.4, 50 rpm

| Time (hours) | % brivaracetam dissolved |
|---|---|
| 0 | 0 |
| 0:15:00 | 101 |
| 0:30:00 | 101 |
| 0:45:00 | 102 |
| 1:00:00 | 102 |

Tablet 4 shows an immediate release of the Brivaracetam that complies with the in vitro dissolution requirements.

Example 3

Tablets C, D, E, F and G are prepared by dry granulation process with the following core compositions (Table 5).

The process is identical to the process described in example 2. After the manufacturing of the tablets cores, the cores are film-coated with an aqueous suspension of Opadry™ white using the adequate equipment in order to have the film-coated tablets.

TABLE 5

Core compositions of tablets C, D, E, F and G

Particles

| | Amount (mg) | | | | |
|---|---|---|---|---|---|
| | C | D | E | F | G |
| Brivaracetam | 5.00 | 10.00 | 10.00 | 25.00 | 50.00 |
| Beta cyclodextrin | 1.35 | 2.70 | 2.70 | 6.75 | 13.50 |
| Lactose monohydrate | 22.5 | 19.40 | 45.00 | 48.50 | 97.00 |
| Sodium croscarmellose | 1.00 | 1.00 | 2.00 | 2.50 | 5.00 |

Blend (external phase)

| Sodium croscarmellose | 1.00 | 1.00 | 2.00 | 2.50 | 5.00 |
| anhydrous lactose | 22.55 | 19.30 | 45.10 | 48.25 | 96.50 |
| Magnesium stearate | 0.6 | 0.60 | 1.20 | 1.50 | 3.00 |

Coating

| Opadry TM white | 2.70 | 2.70 | 5.40 | 6.75 | 13.50 |
| Core tablet mass (mg) | 54 mg | 54 mg | 108 mg | 135 mg | 270 mg |

Opadry®™ white is a film-coating agent used to mask the bitter taste of the active principle ingredient. The amount of the film-coating agent on the tablet cores is about 5% (w/w). The film-coating agent consists of a mixture of hydroxypropylmethylcellulose, Macrogol 4000 (also known as PEG 3350), saccharin sodium, titanium dioxide.

TABLE 6 coated tablet C; results in % of 5 mg brivaracetam immediate release tablets (paddle method, 900 mL phosphate buffer pH 6.4, 50 rpm, performed on 6 tablets)

| | Time (min) | | | |
|---|---|---|---|---|
| | 0 | 5 | 30 | 45 |
| mean (%) | 0 | 88.1 | 100.6 | 101.6 |

TABLE 7 coated tablet D; results in % of 10 mg brivaracetam immediate release tablets (paddle method, 900 mL phosphate buffer pH 6.4, 50 rpm; performed on 6 tablets)

| | Time (min) | | | |
|---|---|---|---|---|
| | 0 | 5 | 30 | 45 |
| mean (%) | 0 | 78.0 | 96.9 | 97.0 |

TABLE 8 coated tablet E: results in % of 10 mg brivaracetam immediate release tablets (paddle method, 900 mL phosphate buffer pH 6.4, 50 rpm; performed on 6 tablets)

| | Time (min) | | | |
|---|---|---|---|---|
| | 0 | 10 | 30 | 45 |
| mean (%) | 0 | 100.1 | 99.8 | 101.0 |

TABLE 9 coated tablet F: results in % of 25 mg brivaracetam immediate release tablets (paddle method, 900 mL phosphate buffer pH 6.4, 50 rpm; performed on 6 tablets)

| | Time (min) | | | |
|---|---|---|---|---|
| | 0 | 10 | 30 | 45 |
| mean (%) | 0 | 86.6 | 99.3 | 100.4 |

TABLE 10 tablet G: results in % of 50 mg brivaracetam immediate release tablets (paddle method, 900 mL phosphate buffer pH 6.4, 50 rpm; performed on 6 tablets)

| | Time (min) | | | |
|---|---|---|---|---|
| | 0 | 15 | 30 | 45 |
| Mean (%) | 0 | 100.0 | 100.7 | 99.8 |

Tablets C, D, E, F and G show an immediate release of the Brivaracetam that complies with the in vitro dissolution requirements.

Example 4

Tablets H and I are prepared by direct compaction process with the following core compositions (Table 13).

TABLE 13 tablets H and I

| Amount (mg) | H | I |
|---|---|---|
| Brivaracetam | 10.00 | 25.00 |
| Beta cyclodextrin | 2.70 | 6.75 |
| Lactose monohydrate | 45.00 | 48.50 |
| Sodium croscarmellose | 2.00 | 2.50 |
| Sodium croscarmellose | 2.00 | 2.50 |
| anhydrous lactose | 45.10 | 48.25 |
| Magnesium stearate | 1.20 | 1.50 |

The main steps of the process for manufacturing tablets are as follows:

Blending the cyclodextrin agent, all the excipients and brivaracetam: the blending operation is achieved using adequate mixer in order to have an homogenous blend.

Compaction: the compaction can be performed using a dry granulator or a tablet machine.

Grinding: the obtained ribbons are then ground.

Compression: the tabletting operation can be performed using a tablet press.

Tablet shows an immediate release of the Brivaracetam that complies with the in vitro dissolution requirements.

TABLE 14 tablet H: results in % of 10 mg brivaracetam immediate release tablets (paddle method, 900 mL phosphate buffer pH 6.4, 50 rpm; performed on 6 tablets)

| | Time (min) | | | |
|---|---|---|---|---|
| | 0 | 15 | 30 | 45 |
| Mean (%) | 0 | 101 | 101 | 101 |

TABLE 15 tablet I: results in % of 25 mg brivaracetam immediate release tablets (paddle method, 900 mL phosphate buffer pH 6.4, 50 rpm; performed on 6 tablets)

| Time (min) | 0 | 15 | 30 | 45 |
|---|---|---|---|---|
| Mean (%) | 0 | 100.0 | 100.0 | 100.0 |

Example 5

Granules are prepared by dry granulation process with the following composition (table 16).

TABLE 16

| Components | Granules % |
|---|---|
| Brivaracetam | 16.7 |
| Lactose monohydrate | 75.4 |
| Beta cyclodextrin | 4.5 |
| Sodium croscarmellose | 3.4 |

The granules comprise the active ingredient, the excipients and the cyclodextrin agent.

The granules are manufactured as follows. The active ingredient, the excipients, and the cyclodextrin agent are mixed using a planetary mixer. The blend is mixed. This pre-blend is then compacted using a roller compactor and the resulting ribbons are sieved in order to obtain the granules.

The granules are put in capsules.

Capsules show an immediate release of the Brivaracetam that complies with the in vitro dissolution requirements.

Example 6

Granules are prepared by dry granulation process with the following composition (table 17).

TABLE 17

| Components | Granules % |
|---|---|
| Seletracetam | 10.3 |
| Anhydrous lactose | 41.2 |
| Lactose monohydrate | 41.2 |
| Beta cyclodextrin | 2.5 |
| Sodium croscarmellose | 3.7 |
| Magnesium stearate | 1.1 |

The granules are prepared as described in example 5.

Capsules show an immediate release of the Seletracetam that complies with the in vitro dissolution requirements.

Example 7

A tablet is prepared by dry granulation process with the following composition (table 18).

TABLE 18

| composition 50 mg | |
|---|---|
| Components | tablet % |
| Brivaracetam | 18.5 |
| Lactose monohydrate | 35.9 |
| Beta cyclodextrin | 5.0 |
| Sodium croscarmellose | 3.7 |
| Magnesium stearate | 1.1 |
| Lactose anhydre | 35.8 |

Test results show that the immediate release tablet complies with the in vitro dissolution requirement.

Example 8

| | Tablet (%) |
|---|---|
| Brivaracetam | 9.2 |
| Lactose monohydrate | 41.5 |
| Betacyclodextrin | 2.5 |
| Sodium Croscarmellose | 3.6 |
| Lactose anhydrious | 41.6 |
| Mg stearate | 1.1 |
| Silicon dioxide colloidal | 0.5 |

The particles comprise the active ingredient, the diluent, the cyclodextrin agent and a part of the disintegrant. The external phase comprises the second part of the disintegrant and the lubricant and the gliding agent.

The particles are manufactured as follows. The brivaracetam as active ingredient, lactose monohydrate, the cyclodextrin agent and the half of the amount of sodium croscarmellose are mixed using a planetary mixer. The blend is mixed. This blend is then compacted using a roller compactor and the resulting ribbons are sieved in order to obtain the particles. The particles are then mixed with the half of the amount of sodium croscarmellose and with the magnesium stearate and the colloidal silica dioxide. The final blend is then compressed on a tablet machine to obtain the tablets cores.

The main steps of the process for manufacturing tablets are as follows:

Blending the cyclodextrin agent, croscarmellose sodium, lactose monohydrate and brivaracetam: the blending operation can be achieved using diffusion mixers, convection mixers and/or pneumatic mixer.

Compaction: the compaction can be performed using a tablet press and/or a dry granulator by slugging or roller compaction.

Grinding: the grinding of the ribbons obtained by dry granulation can be performed using screening mills with a screen opening size comprised between 0.33 mm to 4 mm.

Adding anhydrous lactose, croscarmellose sodium, colloidal silicon dioxide, magnesium stearate.

Blending: the blending operation can be achieved using diffusion mixers, convection mixers and/or pneumatic mixers.

Compression: the tabletting operation can be performed using a tablet press;

Film-coating: this operation can be performed using a pan coater or a gas suspension based coater and more preferably a perforated pan coater.

The disintegration time for the above tablets is 1 minute 53 seconds when determined according to Eur. Ph. 2.9.1. So, test results show that the immediate release tablet complies with the in vitro dissolution requirement.

Example 9

All experiments were performed in accordance with the Guidelines of the local Ethical Committee for Animal Experimentation.

Epileptiform responses in hippocampal slices: Levetiracetam reduces epileptiform responses induced in rat hippocampal slices by high-K+/low-Ca2+ concentrations in the perfusion fluid and induced by bicuculline. The effect of brivaracetam on epileptiform responses induced by high-K+/low-Ca2+ concentrations or by bicuculline was examined in transverse hippocampal slices prepared from Sprague-Dawley rats according to previously reported standard procedures. The epileptiform responses were induced by passing from a normal perfusion of artificial cerebrospinal fluid (ACSF) (K+3 mM; Ca2+2.4 mM) to either high-K+/low-Ca2+ fluid (HKLCF) (K+7.5 mM; Ca2+0.5 mM) or to 5 M bicuculline methiodide (BMI)-containing ACSF.

Extracellular field potentials (FPs) were recorded in the CA3 area of the slices with 2 M NaCl-filled glass microelectrodes. The evoked FPs were recorded at 10-min intervals in response to fimbrial stimulation with constant current rectangular pulses that elicit a single population spike (PS) of 50-75% of the maximal amplitude when the slice is in ACSF. In the HKLCF model, 2 min of spontaneous activity were also recorded, in the middle of each 10-min interval between the recordings of evoked responses.

Either brivaracetam or levetiracetam was added to the bathing fluid of the slices 20 min before shifting from ACSF to either HKLCF or 5 M BMI-containing ACSF, and was kept in the perfusion fluid throughout the experiment.

Audiogenic seizures in mice: Genetically sound-sensitive male mice (16-28 g; n=10 per group), responding with wild running, clonic and tonic convulsions to an acoustic stimulation, were used. Audiogenic seizures were induced by an acoustic stimulus (90 dB, 10-20 kHz) applied for 30 s. The mice were pretreated with either saline, brivaracetam (i.p., 30 min) or levetiracetam (i.p., 60 min), and the proportion of mice protected against clonic convulsions was used as the end point to assess anticonvulsant activity.

Chemically induced seizures in mice: Pentylenetetrazol, 83 mg kg-1 s.c., was used to evaluate the anticonvulsant properties of brivaracetam. The dose was selected based on dose-effect curves in saline-treated animals as the convulsive dose inducing clonic convulsions of all four extremities in 97% of the animals. Immediately after administration of the chemoconvulsant, the mice were placed individually in small plastic cages (25 13 8 cm) and observed for the presence of clonic convulsions in all four extremities, for 60 min. The occurrence of tonic convulsions (hindlimb extension) and mortality was also recorded during this interval. The proportion of mice protected against clonic convulsions was calculated and used as the end point for anticonvulsant activity.

Results

Epileptiform responses in hippocampal slices: Changing the perfusion of rat hippocampal slices from the normal ACSF to HKLCF produced increasingly epileptiform FPs in the CA3 area in response to constant-current fimbrial stimulation. In control slices exposed to HKLCF alone, the PS1 amplitude progressively increased, reaching plateau values within 20 min (4.250.77 mV), nearly twofold higher than those recorded under ACSF perfusion (2.180.15 mV; means.d. for n=10 slices). Also, constant-current single stimuli-evoked bursts of repetitive PSs (that is, PS2, PS3 and so on) increased markedly in number in the first 30 min of HKLCF perfusion from the single PS1 to an average of 7.62.3 PS per evoked burst, and continued to increase slightly up to the end of the records, reaching an average of 8.81.6 PS per evoked burst after 80-min perfusion of HKLCF. Both brivaracetam and levetiracetam reduced these epileptiform responses. Upon 15-min perfusion of HKLCF, spontaneous field bursts occurred in 4 out of the 10 control slices exposed to HKLCF alone, whereas from 25 min in HKLCF to the end of the records, all control slices presented regular field bursting. Brivaracetam (3.2 M), but not levetiracetam (32 M), reduced the rate of this spontaneous bursting.

In vivo studies: In fully amygdala-kindled rats, brivaracetam induced a significant suppression in motor-seizure severity from a dose of 21.2 mg kg-1, whereas levetiracetam induced a similar effect from a dose of 170 mg kg-1. Brivaracetam also significantly reduced the after-discharge duration at the highest dose tested (212.3 mg kg-1), whereas levetiracetam was inactive on this parameter up to 1700 mg kg-1.

Audiogenic seizure-susceptible mice were protected against the expression of clonic convulsions by brivaracetam and levetiracetam. Brivaracetam, administered i.p. 30 min before seizure induction in mice, also protected against clonic convulsions induced by pentylenetetrazol and against tonic hindlimb extension induced by a maximal electroshock in mice, although with higher ED50 values.

Brivaracetam significantly suppressed spontaneous SWDs in GAERS rats from a dose of 2.1 mg kg-1 with complete inhibition appearing at the highest dose tested (67.9 mg kg-1).

Pretreatment with brivaracetam during corneal kindling of mice resulted in a significant reduction in the incidence of generalized motor seizures, and a similar incidence reduction was observed with levetiracetam at higher doses. Continued corneal stimulations following termination of treatment showed a persistent reduction in the incidence of generalized motor seizures in the group previously treated with the highest dose of brivaracetam.

The invention claimed is:

1. An oral pharmaceutical composition consisting of particles and pharmaceutically acceptable additives in a film-coated, immediate release tablet, wherein the particles consist of brivaracetam, a binder which is beta cyclodextrin, a disintegrant which is sodium croscarmellose, and a diluent consisting of lactose monohydrate, anhydrous lactose or a mixture thereof, and the additives consist of sodium croscarmellose, anhydrous lactose and magnesium stearate, wherein the weight of beta cyclodextrin is 1.0 to 8.16% of the total weight of the particles, and
   the weight ratio of the brivaracetam to the beta cyclodextrin is 3.7:1.

2. The oral pharmaceutical composition according to claim 1, wherein the beta cyclodextrin has a water content between 10 and 14% (w/w).

3. The oral pharmaceutical composition according to claim 1, wherein the particles consist of 10.00 mg of brivaracetam, 2.7 mg of beta cyclodextrin, 45 mg of lactose monohydrate, and 2 mg of sodium croscarmellose.

4. The oral pharmaceutical composition according to claim 1, wherein the disintegrant is 0.5 to 25% by weight of the particles.

5. The oral pharmaceutical composition according to claim 4, wherein the diluent is 30-90% by weight of the particles.

6. The oral pharmaceutical composition according to claim 1, wherein the particles consist of 25.00 mg of brivaracetam, 6.75 mg of beta cyclodextrin, 48.50 mg of lactose monohydrate and 2.50 mg of sodium croscarmellose.

7. The oral pharmaceutical composition according to claim 1, wherein the particles consist of 50.00 mg of brivaracetam, 13.50 mg of beta cyclodextrin, 97.00 mg of lactose monohydrate and 5.00 mg of sodium croscarmellose.

8. The oral pharmaceutical composition according to claim 1 wherein the beta cyclodextrin is 2.38 wt % to 5 wt % of the tablet.

9. An oral pharmaceutical composition consisting of particles and pharmaceutically acceptable additives in a film-coated immediate release tablet, wherein
   the particles consist of 10.00 mg of brivaracetam, 2.70 mg of beta cyclodextrin, 45.00 mg of lactose monohydrate and 2.00 mg of sodium croscarmellose; and the additives consist of 2.00 mg of sodium croscarmellose, 45.10 mg of anhydrous lactose and 1.20 mg magnesium stearate in an external phase.

10. An oral pharmaceutical composition consisting of particles and pharmaceutically acceptable additives in a film-coated immediate release tablet, wherein the particles consist of 25.00 mg of brivaracetam, 6.75 mg of beta cyclodextrin, 48.50 mg of lactose monohydrate and 2.50 mg of sodium croscarmellose, and the additives consist of 2.50 mg of sodium croscarmellose, 48.25 mg of anhydrous lactose and 1.50 mg magnesium stearate.

11. An oral pharmaceutical composition consisting of particles and pharmaceutically acceptable additives in a film-coated immediate release tablet, wherein the particles consist of 50.00 mg of brivaracetam, 13.50 mg of beta cyclodextrin, 97.00 mg of lactose monohydrate and 5.00 mg of sodium croscarmellose, and the additives consist of 5.00 mg of sodium croscarmellose, 96.50 mg of anhydrous lactose and 3.00 mg magnesium stearate.

12. An oral pharmaceutical composition consisting of particles and pharmaceutically acceptable additives in a film-coated, immediate release tablet, wherein the particles consist of 10.00 mg of brivaracetam, 2.70 mg of beta cyclodextrin, 45.00 mg of lactose monohydrate, 4.00 mg of sodium croscarmellose, and 45.10 mg of anhydrous lactose, and the additives consist of 1.20 mg of magnesium stearate.

13. An oral pharmaceutical composition consisting of particles and pharmaceutically acceptable additives in a film-coated, immediate release tablet, wherein the particles consist of 25.00 mg of brivaracetam, 6.75 mg of beta cyclodextrin, 48.50 mg of lactose monohydrate, 5.00 mg of sodium croscarmellose, and 48.25 mg of anhydrous lactose, and the additives consist of 1.50 mg magnesium stearate.

14. An oral pharmaceutical composition consisting of particles and pharmaceutically acceptable additives in a film-coated, immediate release tablet, wherein the particles consist of 50.00 mg of brivaracetam, 13.50 mg of beta cyclodextrin, 97.00 mg of lactose monohydrate, 10.00 mg of sodium croscarmellose, 96.50 mg of anhydrous lactose, and the additives consist of 3.00 mg of magnesium stearate.

* * * * *